United States Patent [19]

Wang et al.

[11] Patent Number: 4,735,896

[45] Date of Patent: Apr. 5, 1988

[54] SYNTHETIC PEPTIDE AND PROCESS OF USING SAME FOR THE DETECTION AND DIAGNOSIS OF AIDS AND PRE-AIDS CONDITIONS

[75] Inventors: Chang Y. Wang, New York; James J. G. Wang, Flushing, both of N.Y.

[73] Assignee: United Biomedical, Inc., Lake Success, N.Y.

[21] Appl. No.: 847,102

[22] Filed: Apr. 2, 1986

Related U.S. Application Data

[63] Continuation-in-part of Ser. No. 837,566, Mar. 4, 1986, which is a continuation-in-part of Ser. No. 774,644, Sep. 11, 1985.

[51] Int. Cl.$^4$ .................... C12Q 1/70; G01N 33/53
[52] U.S. Cl. ............................... 435/5; 424/82; 424/89; 435/7; 435/805; 435/810; 436/506; 436/542; 436/808; 436/811; 530/324; 530/325; 530/326; 530/812; 530/815
[58] Field of Search .................... 435/5, 7, 810, 805; 530/326, 324, 325; 424/82, 89; 436/506, 542, 811, 808

[56] References Cited

U.S. PATENT DOCUMENTS

| | | | |
|---|---|---|---|
| 4,075,194 | 2/1978 | Sela et al. | 530/327 |
| 4,529,783 | 12/1985 | Cosand | 530/324 |
| 4,554,101 | 11/1986 | Hopp | 260/112.5 R |

FOREIGN PATENT DOCUMENTS

| | | | |
|---|---|---|---|
| 44710 | 1/1982 | European Pat. Off. | 530/387 |
| 84/04327 | 11/1984 | PCT Int'l Appl. | 435/5 |
| 86/01834 | 3/1986 | PCT Int'l Appl. | 435/5 |

OTHER PUBLICATIONS

Chang et al., Science 228 (4/5/85) 93–96.
N. T. Chang et al., "An HTLV-III Peptide Produced by Recombinant DNA is Immunoreactive with Sera from Patients with AIDS" *Nature*, vol. 315, 151–154 (May 9, 1985).
D. Pauletti et al., "Application of Modified Computer Algorithm in Determining Potential Antigenic Determinants Associated with the AIDS Virus Glycoprotein", *Anal. Biochem*, 151, 540–546 (1985).

*Primary Examiner*—Christine M. Nucker
*Attorney, Agent, or Firm*—Morgan & Finnegan

[57] ABSTRACT

The present invention relates to a method for the detection and diagnosis of AIDS (acquired immune deficiency syndrome) ARC (AIDS Related Complex) and pre-AIDS conditions in body fluids by the use of a chemically synthesized peptide. The peptide has an amino acid sequence corresponding to a segment of the envelope protein, p41, of HTLV-III and has been found to be highly immunoreactive with antibodies in sera of patients with AIDS, ARC and pre-AIDS conditions. More specifically, the present invention is directed to the use of a chemically synthesized peptide containing therein a segment of about twenty-one (21) amino acids, or their analogues, in a prescribed sequence for the detection of antibodies to the HTLV-III virus in human body fluids of AIDS, ARC or pre-AIDS patients. The detection method includes an enzyme-linked immunosorbent assay (ELISA), an immunoradiometric assay (IRMA), and other forms of immuno assay procedures such as enzyme immuno blotting assay on nitrocellulose paper and hemagglutination assay using the peptide as the antigen. The preferred detection method is ELISA.

The present invention also relates to a vaccine and a method for generating antibodies to HTLV-III in healthy mammals, including humans by the use of the chemically synthesized 21mer peptide or its analogues.

17 Claims, 1 Drawing Sheet

SYNTHETIC PEPTIDE AND PROCESS OF USING SAME FOR THE DETECTION AND DIAGNOSIS OF AIDS AND PRE-AIDS CONDITIONS

CROSS REFERENCE TO RELATED APPLICATIONS

This is a continuation-in-part application of application Ser. No. 837,566, filed Mar. 4, 1986, which is in turn a continuation-in-part application of application Ser. No. 774,644, filed Sept. 11, 1985.

INTRODUCTION

The present invention relates to a high sensitive method for the detection of antibodies to HTLV-III in body fluids and diagnosis of AIDS (acquired immune deficiency syndrome) ARC (AIDS Related Complex) and pre-AIDS conditions by the use of a chemically synthesized peptide, a vaccine for AIDS, ARC or pre-AIDS conditions and a method for stimulating the production of antibodies to HTLV-III to provide protection against infection by HTLV-III or LAV in healthy mammals, including humans. The amino acid sequence of the peptide corresponds to a segment of the envelope protein, p41, of HTLV-III and has been found to be highly immunoreactive with antibodies in sera of patients with AIDS, ARC and pre-AIDS conditions. More specifically, the present invention is directed to the use of a chemically synthesized peptide containing therein a segment of about twenty-one (21) amino acids, or their analogues, in a prescribed sequence for the detection of antibodies to the HTLV-III virus in human body fluids of AIDS, ARC or pre-AIDS patients. The detection method includes an enzyme-linked immunosorbent assay (ELISA) and an immunoradiometric assay (IRMA) and other methods of immuno assay procedures such as enzyme immunoblotting on nitrocellulose paper and hemagglutination using the peptide as the antigen. The preferred detection method is ELISA.

BACKGROUND OF THE INVENTION

Acquired immune deficiency syndrome (AIDS) has been recently recognized in several countries. Due to its devastating effect on the patients and indications that the disease is spreading, much effort has been devoted to elucidate and identify the cause of the disease. Epidemiologic data suggests that AIDS is caused by an infectious agent that is horizontally transmitted by intimate contact or exposure to blood or certain blood products.

In 1983, F. Barre-Sinoussi et al. of the Institute Pasteur reported the isolation of a T-lymphotropic retrovirus from a patient at risk for AIDS. The retrovirus appeared to be a member of the human T-cell leukemia virus (HTLV) family. However, its immunological response is distinct from known HTLV-I or HTLV-II. F. Barre-Sinoussi et al., Science, 220, pp. 868 (May, 1983).

A similar virus, designated HTLV-III, has also been isolated by R. C. Gallo's group at National Cancer Institute from the blood samples of a large number of AIDS and ARC patients by co-cultivation with a permissive T-cell line H9. See Popovic, M. et al., Science, 224, pp. 497 (1984) and Gallo, R. et al., Science, 224, pp. 500 (1984).

V. S. Kalyanaraman et al. of the Center for Disease Control, Atlanta, Ga., reported the isolation of a lymphadenopathy associated virus (LAV) in patients with AIDS and the development of a radioimmuno-precipitation assay using the major core protein, p25, of LAV. Their test procedure involved the use of the LAV virus propagated in primary cultures of blood lymphocytes and harvested. The p25 core protein was isolated from the harvested virus, labelled with $I^{125}$ and used as target antigen. The labelled antigen was added to serum and precipitation of at least 15% of the labelled antigen is regarded as a positive result. See V. S. Kalyanaraman et al., Science, 225, pp. 321 (July 1984). However, based on the reported results, the test was positive only for 41% of the AIDS patients and 72% positive for patients with lymphadenopathy syndrome (LAS) otherwise known as ARC. This means that the procedure is not sufficiently sensitive or accurate to be used as a detection or diagnostic tool for screening serum for the presence of antibodies to the AIDS virus.

LAV and HTLV-III, as well as various strains of related retrovirus isolated from AIDS patients share several important characteristics. See Feorino, P. et al., Science, 225, pp. 69 (1984); Levy, J. et al., Science, 225, pp. 840 (1984). These include viral replication in OKT4+ human T-cell leukocytes, in vivo and in vitro; association with impaired T-cell proliferation, the appearance of cytopathic effects; (See Montagnier et al., *Human T Cell Leukemia Virus*, pp. 363, Cold Spring Harbor Laboratory, 1984; Popovic, M. et al., op. cit., and Klatzmann, D. et al. Science, 225, pp. 59 (1984)) and recognition by antibodies in the sera of AIDS and ARC patients. See Montagnier, et al., op. cit.; Levy J. et al., op. cit., Sarngadharan, M. et al., Science, 224, pp. 505 (1984); Safai, B. et al., Lancet, i, pp. 1438 (1984); Brun-Vezinet, F., et al., Lancet, i, pp. 1253 (1984); Brun-Vezinet, F. et al., Science, 226, pp. 453 (1984); Goldbert, J. et al., Lancet, ii, pp. 711 (1984) and Laurence J. et al., New England J. Med., 311, pp. 1269 (November 1984).

In November 1984, L. W. Kitchen et al. reported the use of a HTLV-III infected line, designated H9/HTLV-III, to test the incidents of AIDS in haemophiliac patients. The method involved inactivation of the virus with 2% paraformaldehyde in phosphate buffer and used of the inactivated cells to determine if haemophiliac patients have been inadvertently exposed to AIDS virus through blood transfusion. The data using sera samples from 50 haemophiliacs show that there is an increasing risk for these patients to contract AIDS, because of their need for blood transfusions to sustain life. L. W. Kitchen et al., Nature, 312, pp. 367 (November 1984). This means that there is an urgent need for a safe, reliable and sensitive test to screen each blood sample before its inclusion in blood banks to isolate blood samples which have been contaminated with AIDS virus, and thus avoid the inadvertent spread of AIDS among patients who must receive blood transfusions, e.g. haemophiliac and surgical patients.

In November 1984 and January 1985, R. C. Gallo's group at National Cancer Institute and other collaborators positively concluded that HTLV-III is the causative agent of AIDS and reported the nucleotide sequence of HTLV-III. See Beatrice Hahn et al., Nature, 312, pp. 166 (November 1984), George M. Shaw et al., Science, 226, pp. 1165 (December 1984) and Lee Ratner et al., Nature, 313, pp. 277 (January 1985).

Meanwhile, three other groups also reported the complete nucleotide sequence of the AIDS virus. See Muesing et al., Nature, 313, pp. 450 (February 1985); Sanchez-Pescados, R. et al., Science, 227, pp. 484 (February 1985) and Wain-Hobson et al., Cell, 40, pp. 9

(January 1985). These reports elucidated the structure of the HTLV-III virus at both the DNA level and the projected protein level and permit further serological studies of the different epitopes present on the HTLV-III virus.

Simultaneously, the group at Institute Pasteur reported that LAV has been identified as a causative agent for AIDS, and is considered to be identical to HTLV-III. The assay procedure used by this group also involves propagating LAV in T4+ cells of healthy individuals. The viral antigen was then concentrated and deactivated in 0.5 percent sodium dodecyl sulfate at 37° C. for 15 minutes. Serum samples were then tested against the antigen in an enzyme immunoassay with orthophenylene diamine as substrate. The presence of antibody in serum was found in 68% of AIDS patients, 100% of patients with Kaposi's sarcoma and 100% of pre-AIDS patients. Jeffrey Laurence et al., op. cit.

Recently, U.S. Pat. No. 4,520,113 was issued to R. C. Gallo et al. The Gallo et al. patient describes a method of detecting antibodies in sera of AIDS and pre-AIDS patients by using lysates of a cell line, designated H9/HTLV-III, as the antigen in an enzyme-linked immunosorbent assay (ELISA) or in a strip radioimmunoassay based on the Western Blot technique or an indirect immunofluorescent method. The method is about 85% accurate. The Gallo patent further indicated that several antigens from HTLV-III, p65, (MW 65,000), p60 (MW 60,000), p55 (MW 55,000), p24 (MW 24,000) and p41 (MW 41,000) are recognized by antibodies in sera from AIDS patients, homosexuals and heroin addicts. Of these, major immune reactivity or specificity is directed against p41, a protein constituting the envelope antigen of HTLV-III. This patent further states that it is believed that additional purification and refinement of p41 may lead to an even more sensitive ELISA assay. Based on this statement, the antigen suitable as a test reagent is to be a p41 segment derived from HTLV-III cultivated in H9 cell line.

It is further reported in Robert C. Gallo et al., *Science*, 228, pp. 93 (April 1985) that a combined cloning and expression system in *E. coli* has been used to identify HTLV-III encoded peptides which react immunologically with antibodies in sera from AIDS patients. Closed HTLV-III DNA was sheared into fragments and inserted into an expression vector. The inserted DNA was then expressed in *E. coli* transformants. Of 300 clones tested, 20 showed specific reactivity with sera from AIDS patients. The 20 clones were analyzed and found to contain segments from the ORF segment of HTLV-III and were identified as clones 175, 191, 13, 31, 162, 113, 121 and 127. Of the eight clones, ORF clones 113, 121 and 127 define the protein encoded by the portion of the env-lor region produced by HTLV-III infected cells and induces antibody production in most if not all AIDS patients.

All of the reported assay procedures for detecting antibodies to HTLV-III and for diagnosis of AIDS or pre-AIDS conditions involve the use of the HTLV-III or LAV virus. None of the procedures are 100% accurate. This is undesirable for use in the screening of sera in blood banks. The less than 100% accuracy of the tests may permit contaminated sera from escaping detection and be used in blood transfusions to the severe detriment of blood recipients. Moreover, the use of the HTLV-III virus as the testing agent is dangerous to healthy laboratory workers, requiring extreme precautions to avoid all chances of exposure during the preparative process to make the test reagent. Furthermore, even though the deactivated virus is used in some of the published procedures, exposure to the deactivated virus can cause antibody production in healthy workers, who may then be falsely diagnosed as having AIDS, ARC or pre-AIDS condition. Moreover, presence of cellular materials from H9 cells or *E. coli* in the test agent may elicit a false positive response in the HTLV-III antibodies screening test from individuals who have antibodies to *E. coli* or H9 cells. These false positive reactions can bring severe anxiety to the healthy individuals and their family and may lead to a healthy individual being mistakenly diagnosed as having AIDS and be exiled from normal social activities as a consequence.

Furthermore, up to the present, no viable vaccine or method to provide protection against HTLV-III has been reported for AIDS, ARC or pre-AIDS conditions. The use of deactivated virus provokes fears of contracting the disease and would prevent its acceptability and use.

Similarly, the development of monoclonal and polyclonal antibodies to HTLV-III in mammals involves the use of HTLV-III as the immunogen and this presents similar risks in the procedure.

It is, therefore, an objective of the present invention to develop a detection or diagnostic procedure that does not require the use of the virus or lysates thereof as a test reagent.

A further objective is to develop a test procedure that is highly sensitive and accurate, preferably 100% accurate.

Another objective is to develop a test that is highly sensitive so that very little test reagent or body fluid is needed to obtain an accurate result.

A further objective is to prepare a test reagent by chemical means, which test reagent can be used to detect the presence of antibodies to HTLV-III in body fluids and diagnose AIDS, ARC or pre-AIDS conditions, thereby avoiding the danger of exposure to the virus or segments thereof and the unnecessary proliferation of the virus.

Another objective is to develop a vaccine which when introduced into the body will stimulate production of antibodies to HTLV-III to provide protection against infection by HTLV-III or LAV in healthy mammals, including humans.

A further objective is to provide an immunogen which can be used for the development in mammals of monoclonal and polyclonal antibodies to HTLV-III which does not involve the use of HTLV-III as the immunogen.

BRIEF DESCRIPTION OF THE INVENTION

According to the present invention, a peptide with about twenty one amino acids arranged in a specific sequence has been made by solid phase peptide synthesis. The 21mer peptide has been found to be useful in a highly sensitive and accurate method for the detection of antibodies to HTLV-III in sera and body fluids and diagnosis of AIDS, ARC or pre-AIDS conditions. The 21mer peptide has also been found to be useful in stimulating production of antibodies to HTLV-III or LAV in healthy mammals such as Balb/c mice.

According to the present invention, a peptide useful for the detection of antibodies to HTLV-III and diagnosis of AIDS, ARC or pre-AIDS conditions in sera or body fluids is selected from the group of peptides comprising:

Arg-Ile-Leu-Ala-Val-Glu-Arg-Tyr-Leu-Lys-Asp-Gln-Gln-Leu-Leu-Gly-Ile-Trp-Gly-Cys-Ser, analogues thereof and segment thereof; wherein:
Ala=alanine,
Arg=arginine,
Asp=aspartic acid,
Gln=glutamine,
Glu=glutamic acid,
Leu=leucine,
Lys=lysine,
Gly=glycine,
Ile=isoleucine,
Ser=serine,
Trp=trypotphan,
Tyr=tyrosine,
Val=valine, and
Cys=cysteine.

The highly sensitive and accurate method of detecting antibodies to HTLV-III in body fluids and diagnosis of AIDS, ARC or pre-AIDS condition comprises the following steps:

A. Preparing a peptide selected from the group comprising:
Arg-Ile-Leu-Ala-Val-Glu-Arg-Tyr-Leu-Lys-Asp-Gln-Gln-Leu-Leu-Gly-Ile-Trp-Gly-Cys-Ser, analogues thereof and segmens thereof, wherein:
Ala=alanine
Arg=arginine
Asp=aspartic acid
Gln=glutamine,
Glu=glutamic acid,
Leu=leucine,
Lys=lysine,
Gly=glycine,
Ile=isoleucine,
Set=serine,
Trp=trypotphan,
Tyr=tyrosine,
Val=valine, and
Cys=cysteine;

B. Using about 0.1 ug to about 20 ug per test of the peptide in a buffer at a pH of about 7 to 10 as the antigen in an immuno assay procedure.

Further, according to the present invention, the peptide when coupled to a protein or a polymer carrier can be used to stimulate production of antibodies to HTLV-III or LAV in healthy mammals including humans. The method comprises introducing an effective amount of the 21mer peptide conjugated to a protein, such as human serum albumin into the body of a healthy mammal by intraperitoneal or subcutaneous injection.

DETAILED DESCRIPTION OF THE INVENTION

Figure 1:
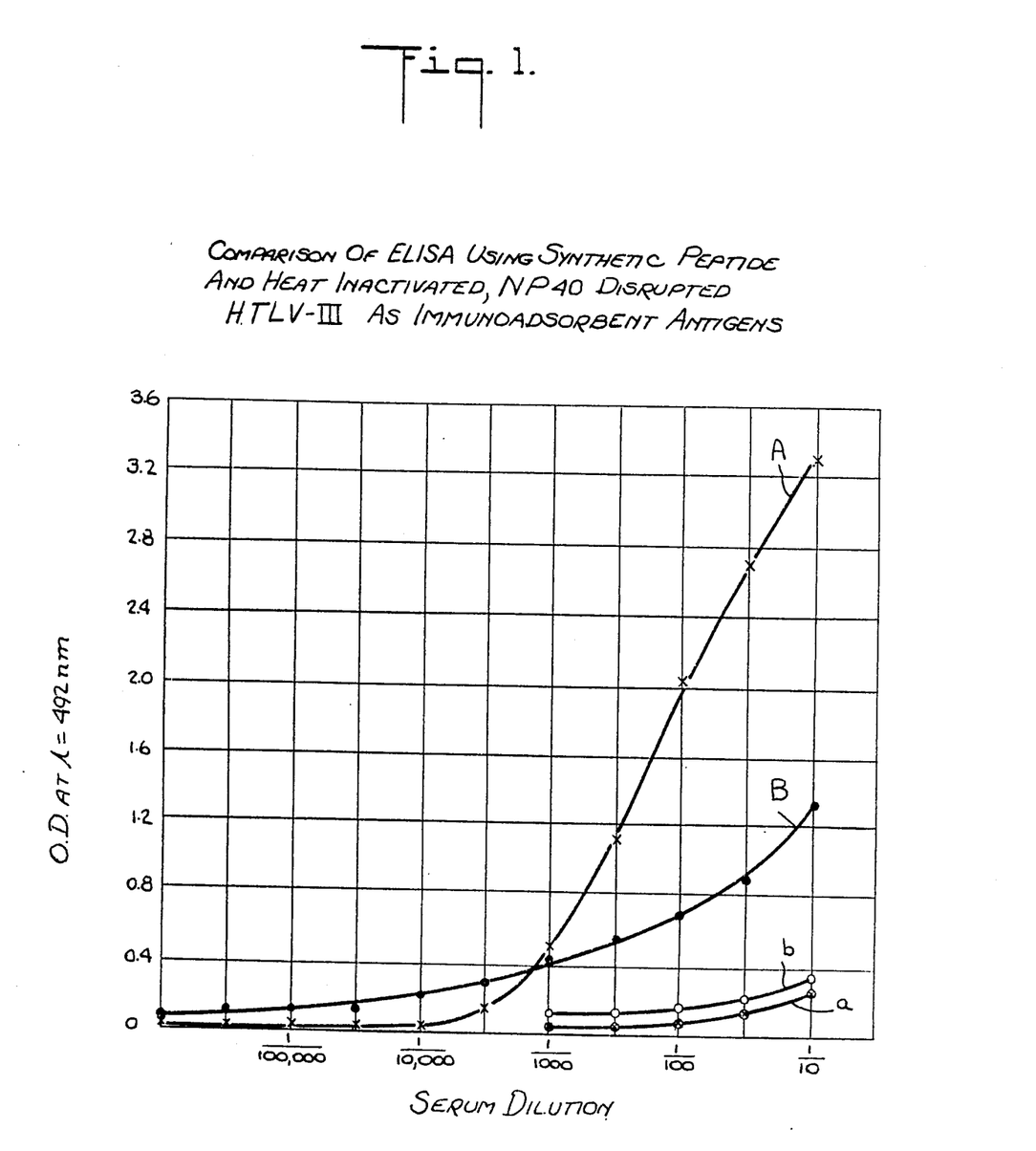
FIG. 1 is a graph comparing the data obtained with sera from AIDS patients using ELISA method wherein the well plates are coated with (A) the peptide of the present invention, (B) deactivated HTLV-III virus; and normal sera with (a) the peptide of the present invention (b) deactivated HTLV-III virus.

In accordance with the present invention a peptide has been chemically synthesized for the detection of antibodies to HTLV-III in body fluids and diagnosis of AIDS, ARC and pre-AIDS condition, for the vaccination of healthy mammals by stimulating the production of antibodies to HTLV-III or LAV in healthy mammals, and for the development of both monoclonal and polyclonal antibodies to HTLV-III in mammals. The peptide comprise about twenty one amino acids or their analogues arranged in the following sequence:

Arg-Ile-Leu-Ala-Val-Glu-Arg-Tyr-Leu-Lys-Asp-Gln-Gln-Leu-Leu-Gly-Ile-Trp-Gly-Cys-Ser wherein Arg is arginine, Ala is alanine, Val is valine, Glu is glutamic acid, Tyr is tyrosine, Lys is lysine, Asp is aspartic acid, Gln is glutamine, Leu is leucine, Gly is glycine, Ile is isoleucine, Trp is tryptophan, Ser is serine and Cys is Cysteine. The peptide may comprise a shorter or longer peptide chain by having more amino acids added to the terminal amino acids, -Arg- or -Ser-, of the above sequence or having a few less of the terminal amino acids from either terminal.

It is expected that as long as the three dimensional conformation recognizable by the dominant antibodies to HTLV-III is preserved, the synthetic peptide may comprise analogues of the recited amino acids of the above sequence or be extended by the addition of amino acids to either terminal or it may be reduced by the deletion of a few of the terminal amino acids to at least about fifteen amino acids. In addition, it is expected that polymeric forms of the 21mer peptide or its analogues can also be used to elicit production of antibodies to HTLV-III.

The amino acid sequence of the polypeptide useful as a test reagent for the detection of antibodies to HTLV-III in body fluids and diagnosis of AIDS, ARC and pre-AIDS condition is prepared to correspond to a partial segment of the amino acid sequence of the HTLV-III virus designated as p41, a part of p120, the LOR (long open reading) segment, defining the envelope protein of the HTLV-III virus.

The peptide useful as a solid phase immunoadsorbent for the detection of antibodies HTLV-III was synthesized by "classical" Merrifield method of solid phase peptide synthesis according to the following scheme.

Following the above scheme, Boc-amino acids are added to the resin to prepare the 21mer peptide according to the following sequence:

| | | |
|---|---|---|
| 1. Boc—Ser | 8. Boc—Leu | 15. Boc—Arg |
| 2. Boc—Cys | 9. Boc—Gln | 16. Boc—Glu |
| 3. Boc—Gly | 10. Boc—Gln | 17. Boc—Val |
| 4. Boc—Trp | 11. Boc—Asp | 18. Boc—Ala |
| 5. Boc—Ile | 12. Boc—Lys | 19. Boc—Leu |
| 6. Boc—Gly | 13. Boc—Leu | 20. Boc—Ile |
| 7. Boc—Leu | 14. Boc—Tyr | 21. Boc—Arg |

Analogues of the 21mer peptide can be prepared by varying the above sequence either by adding or subtracting desired Boc-amino acid(s). The term "analogues" of the 21mer peptide encompasses the entire 21mer peptide, portions thereof, peptides that contain substitutions of amino acid residues, or peptides that contain insertions and/or deletions of amino acids in the 21mer peptide.

Following completion of assembly of the desired blocked peptide on the resin, the peptide-resin is treated with anhydrous hydrofluoric acid to cleave the benzyl ester linking the peptide to the resin in order to liberate the peptide. Side-chain functional groups of amino acids which are blocked during synthesis by benzyl-derived blocking groups are also cleaved from the peptide simultaneously. The free peptide is then analyzed and purified by reverse phase high pressure liquid chromotography (HPLC) and characterized biochemically by amino acid analysis.

Similarly, synthesis of the 21mer peptide that has an amide group on its C-terminal end can be achieved by using a 4-methylbenzhydrylamine resin according to the following scheme:

Coupling the C—terminal Residue to 4-Methylbenzhydryl amine residue

The peptide synthesized according to the above described procedure is highly reactive to antibodies to HTLV-III and can be used as a highly sensitive and specific immunoadsorbent for the detection of antibodies against HTLV-III. Results obtained with the peptide according to the present invention show that it is more sensitive and specific to antibodies against HTLV-III in body fluids than the lysate of density banded HTLV-III itself reported in U.S. Pat. No. 4,520,113. See Table II.

Based on the high degree of sensitivity and specificity of the peptide according to the present invention in the immunoreaction to antibodies to HTLV-III, it is believed that it may also be useful as a vaccine for AIDS, ARC or pre-AIDS conditions, and as an immunogen for the development of both monoclonal and polyclonal antibodies to HTLV-III in mammals. The peptide itself or when coupled to a protein or a polymer carrier, can be introduced to normal subjects to stimulate production of antibodies to HTLV-III, and provide protection against infection by HTLV-III or LAV in healthy individuals. Since the peptide according to the present invention is not derived biochemically from the virus, there is no danger of exposing the normal subjects who are to be vaccinated to the disease.

It has been found that when the 21mer peptide conjugated to human serum albumin (HSA), as the carrier protein, was injected intraperitoneally and subcutaneously into healthy Balb/c mice, antibodies to the 21mer peptide cross reactive with HTLV-III were produced by the Balb/c mice. This is exemplified in Example 7.

Based on the results obtained in Example 7, the 21mer peptide can be used as an immunogen for the development of both monoclonal and polyclonal antibodies to HTLV-III in mammals.

The advantages of using the peptide according to the present invention are many.

The peptide is chemically synthesized. This means that there is no involvement with the HTLV-III virus at any time during the process of making the test reagent or the vaccine. During the preparation of the vaccine or the vaccination process, there is no risk of exposure of the production workers, individuals in the health profession and those being vaccinated to the HTLV-III virus. Similarly, there is no risk of exposure to HTLV-III in the use of the 21mer peptide for the development of monoclonal or polyclonal antibodies to HTLV-III in mammals. Further, up to the final step of the test to detect antibodies to HTLV-III, where the test reagent is exposed to the samples of sera or body fluid, there is no risk of exposure of the laboratory worker to the HTLV-III virus. And, risk of exposure in this final step can be avoided by taking the precautionary step of deactivating any virus which may be present by heating at 56° C. for half an hour the samples of sera or body fluids which are to be tested.

Another problem which is avoided by the process of the present invention is the possibility of false positive results caused by the presence of antigenic material from H9 cells co-purified with the HTLV-III viral preparation or *E. coli* derived proteins co-purified with expressed viral fragments. Certain normal individuals have antibodies to *E. coli* or human leukocyte antigens, e.g. HLA, which are cross reactive with the antigenic materials from H9 cells. Sera samples from these normal individuals may show a positive response in the ELISA or IRMA test even though they have not been exposed to HTLV-III. A diagnosis that a person may be inflicted with AIDS based on this type of false positive response can bring severe anxiety to the person and his/her family, and cause him/her to be excluded from normal social activities. All of these problems can be avoided by using the peptide of the present invention as the test reagent.

Further, with appropriate amino acid analogue substitutions, it is expected that various peptide analogues based on the prescribed amino acid sequence can be synthesized with properties giving rise to lower background readings or better adsorption capacity to solid phases useful for HTLV-III antibodies screening assays.

Various peptide analogs based on the above described amino acid sequence have been prepared. These analogs and their reactivities with the anti HTLV-III antibodies present in sera of AIDS and ARC patients are described in Example 8 and Table VI. The reactivity in an ELISA test for the same amount of each peptide by weight per volume was compared with the reactivity of the 21mer peptide, which was assigned a reactivity of 100.

Our results indicate that the 21mer peptide of the present invention is unique in its size and sequence in that mere deletion of Arg, or -Ile- from the N-terminal or -Trp-Gly-Cys-Ser from the C-terminal, or cleaving this peptide in between the -Lys- and -Asp- to form two peptides of 10 and 11 amino acids, all resulted in dramatic loss of antigenicity conferred by the 21mer peptide. In addition, -Lys- at position 12 from the C-terminal also appear to be important, in that addition of -Lys- to the above said 11-mer peptide restores significantly the antigenicity.

Moreover, because the peptide of the present invention is synthetically prepared, the quality can be controlled and as a result, reproducibility of the test results can be assured. Also, since very small amounts of peptide are required for each test procedure, and the expense of preparing the peptide is relatively low, the cost of screening body fluids for antibodies to HTLV-III and diagnosis of AIDS, ARC or pre-AIDS and the preparation of a vaccine is relatively low.

The peptide prepared in accordance with the present invention can be used to detect HTLV-III infection and diagnose AIDS, ARC and pre-AIDS condition by using it as the test reagent in an enzyme-linked immunosorbent assay (ELISA), an enzyme immunodot assay, a hemagglutination assay or a radioimmunoradiometric assay (IRMA), preferably ELISA. The ELISA technique is exemplified in Example 1, the IRMA technique is exemplified in Example 3, and the hemagglutination assay in Example 3A and 5A.

It is to be noted that in the following methods, 0.25% by weight of glutaldehyde may be added in the coating buffer to facilitate better peptide binding onto the plates or beads. Further, horseradish peroxidase conjugated mouse monoclonal anti human IgG antibody may be used in place of horseradish peroxidase conjugated goat anti human IgG (Fc) as a second antibody tracer.

EXAMPLE 1

Detection of Antibodies to HTLV-III by an Enzyme-Linked Immunoadsorbent Assay Wells of 96-well plates were coated at 4° C. overnight (or 3 hours at room temperature), with the 21mer peptide, prepared as described, at 0.5 ug per well in 100 ul 10 mM $NaHCO_3$ buffer, ph 9.5. The wells were washed three times with phosphate buffered saline (PBS) and then incubated with 250 ul of 3% by weight gelatin in PBS at 37° C. for 1 hour to block non-specific protein binding sites, followed by three more washes with PBS containing 0.05% by volume Tween 20. The test sera (blood taken from a human patient or normal individual) were diluted with PBS containing 20% by volume normal goat serum, 1% by weight gelatin and 0.05% by volume Tween 20 at dilutions of 1:20 and 1:200, volume to volume, respectively. 200 ul of the diluted sera were added to each well and allowed to react for 1 hour at 37° C. The wells were then washed three times with 0.05% by volume Tween 20 in PBS in order to remove unbound antibodies. Horseradish peroxidase conjugated goat anti human IgG (Fc) was used as a second antibody tracer to bind with the AIDS antibody-antigen complex formed in positive wells. 100 ul of peroxidase labeled goat anti-human IgG at a dilution of 1:3000 in 1% by volume normal goat serum, 0.05% by volume Tween 20 in PBS was added to each well and incubated at 37° C. for another hour.

The wells were washed five times with 0.05% by volume Tween 20 in PBS to remove unbound antibody and reacted with 100 ul of the substrate mixture containing 0.04% by weight orthophenylenediamine (OPD) and 0.012% by volume hydrogen peroxide in sodium citrate buffer, pH 5.0. This substrate mixture was used to detect the peroxidase label by forming a color product. Reactions were stopped by the addition of 50 ul of 2.5M $H_2SO_4$ and the color yield measured using an ELISA reader which quantifies the color reading at 492 nm (i.e. OD was measured at 492 nm). Assays were performed in duplicate with two sera dilutions (1:20 and 1:200 respectively). Normal serum samples were used as negative controls. Absorbance readings greater than the average readings +4 SD (standard deviation) of 90 normal sera samples were taken as positive. The results are shown in Table I.

TABLE I

Detection of Antibodies to HTLV-III by
ELISA* using 21mer Peptide as Solid Phase Immunoadsorbent

| | Subject | No. Positive/ No. Tested | Percent Positive |
|---|---|---|---|
| 1. | Patients with AIDS | 98/100 | 98.0% |
| 2. | Patients with ARC | 90/105 | 85.7% |
| 3. | Healthy homosexuals | 17/65 | 26.2% |
| 4. | Patients with Hepatoma | 0/2 | 0% |
| 5. | Patients with autoimmune diseases | 0/51 | 0% |
| 6. | Patients with Primary Immune Deficiency+ | 2/123 | 1.6% |
| 7. | Patients with Lymphatic Leukemias | 0/20 | 0% |
| 8. | Normal subjects | 0/90 | 0% |

*Assay was performed using sera at 1:20 (v/v) dilution with buffer.
+Two sera from this control patient group showed only borderline reactivity.
Note:
Sera from patients with AIDS, ARC, Primary Immunodeficiency, Leukemia/Lymphomas and normal individuals were kindly provided by Drs. S. Gupta at the University of California at Irvine; S. Cunningham-Rundels at Memorial Sloan-Kettering Cancer Center Blood Bank, New York; and J. Gold at the Infectious Disease Unit, Memorial Sloan-Kettering Cancer Center, New York. Sera from patients with autoimmune diseases including Rheumatoid Arthritus, Systemic Lupus Erythematosus and allergies were kindly provided by Dr. N. Chiorazzi at the Rockerfeller University Hospital, New York. Sera from patients with hepatoma were provided by Dr. King-Jen Chang of the National Taiwan University Hospital.

The results in Table I show that the ELISA test procedure according to the present invention with 534 sera samples show that the method is very accurate and highly specific. No immunoreactivity was found in normal subjects or patients who were identified as not being inflicted with AIDS or ARC.

It is to be noted that in screening tests to exclude virus contaminated blood from blood banks, the criteria for defining positive reactions can be made more stringent. For example, instead of regarding average reading of normal sera samples +4 SD as positive, it can be changed to having samples with readings equal to average reading of normal sera samples +2 SD be regarded as positive.

EXAMPLE 2

The procedure of Example 1 was repeated using the same sera samples as in Example 1 except that the well plates were precoated with heat inactivated NP40 solubilized HTLV-III according to Gallo et. al. U.S. Pat. No. 4,520,113. The results are presented in Table II.

TABLE II

Detection of Antibodies to HTLV-III by
ELISA Using Heat Inactivated NP40
Solubilized HTLV-III as Solid Phase Immunoadsorbent

| | | No. Positive/ No. Tested* | | Percent Positive | |
|---|---|---|---|---|---|
| | Subject | NS + 3SD | NS + 4SD | NS + 3SD | NS + 4SD |
| 1. | Patients with AIDS | 64/100 | 46/100 | 64.0% | 46.0% |
| 2. | Patients with ARC | 68/105 | 58/105 | 64.8% | 55.2% |
| 3. | Healthy homosexuals | 9/65 | 7/65 | 13.8% | 10.8% |
| 4. | Patients with autoimmune diseases | 3/51 | 1/51 | 5.9% | 2.0% |
| 5. | Patients with primary immune deficiency | 3/123 | 0/123 | 2.4% | 0% |
| 6. | Normal individuals | 0/90 | 0/90 | 0% | 0% |

*Results were based on average NS (normal sera) + 3 SD and + 4SD, SD = standard deviation.

In comparison with results obtained in Example 1, this method is much less accurate and is therefore, less reliable.

EXAMPLE 3

Detection of Antibodies to HTLV-III by an Immunoradiometric Assay (IRMA)

Wells of 96-well flexible-polyvinylchloride (PVC) plates are coated at 4° C. overnight (or 3 hours at room temperature) with the 21mer peptide, prepared as described, at 0.5 ug per well in 100 ul 10 mM $NaHCO_3$ buffer, pH 9.5. The wells are washed three times with phosphate buffered saline (PBS) and then incubated with 250 ul of 3% by weight gelatin in PBS at 37° C. for 1 hour to block non-specific protein binding sites, followed by three more washes with PBS containing 0.05% by volume Tween 20. The test sera (blood taken from a human patient or normal individual) are diluted with PBS containing 20% by volume normal goat serum, 1% by weight gelatin and 0.05% by volume Tween 20 at dilutions of 1:20 and 1:200 (volume to volume) respectively. 200 ul of the diluted sera are added to each well and allowed to react for 1 hour at 37° C. The wells are then washed three times with 0.05% by volume Tween 20 in PBS in order to remove unbound antibodies. $I^{125}$ labeled affinity purified goat anti human IgG (Fc) is used as a second antibody tracer that binds with the antibody-antigen complex formed in positive wells. 100 ul of $I^{125}$ labeled goat anti-human IgG of 50,000–200,000 cpm in 1% by volume normal goat serum, 0.05% by volume Tween 20 in PBS was added to each well and incubated at 37° C. for another hour.

The wells are washed five times with 0.05% by volume Tween 20 in PBS to remove unbound second antibody and dried. The wells are cut and counted by a gamma-scintillation counter. Assays are performed in duplicate with two sera dilutions, 1:20 and 1:200, volume to volume, respectively. Normal sera sample as negative controls were also tested simultaneously. Cpm readings greater than the average readings of normal sera samples +4 SD (standard deviation) are taken as positive.

EXAMPLE 3A

Detection of Antibodies to HTLV-III by a Hemagglutination Assay using 21-mer Peptide Coated Gelatin Particles, Sheep Red Blood Cells or Latex Beads as Solid Phase Immunoadsorbent One ml thoroughly washed sheep red blood cells, gelatin particles, or polystyrene latex beads are coated with the 21mer peptide at an concentration in the range of 5 ug/ml to 1 mg/ml. The 21mer peptide coated cells, particles or beads are then incubated with serially diluted serum samples in the wells of a 96-well U-shaped microplate. After being left at room temperature for about an hour, the agglutination patterns on the bottom are read, and the largest dilution showing a positive reaction is recorded.

This is a one-step assay which could be used for both qualitative and quantitative analysis of the presence of anti-HTLV-II antibodies in specimens including sera or biofluids.

EXAMPLE 4

A diagnostic AIDS, ARC and pre-AIDS specific test kit for HTLV-III antibodies detection can be constructed. The test kit comprises a compartmented enclosure containing multiple 96-well plates coated prior to use with 0.5 ug of the peptide of the present invention in 100 ul pH 9.5 10 mM NaHCO$_3$ buffer per well. The kit further comprises materials for enzyme detection in separate sealed containers consisting of: (1) normal human serum (as negative control); (2) heat inactivated, NP40 solubilized AIDS serum (as positive control); (3) normal goat serum; (4) peroxidase labelled-goat anti-human IgG; and (5) a color change indicator consisting of orthophenylenediamine (OPD) and hydrogen peroxide in phosphate citrate buffer. The procedure described in Example 1 is to be followed.

In this test kit, 96-well plates, precoated with the peptide of the present invention, can be replaced by polystyrene beads, or multiple mini-columns filled with controlled pore size glass beads, or nitrocellulose paper strip precoated with the peptide of the present invention for use as the solid phase immunoadsorbent.

EXAMPLE 5

A second test kit for detecting antibodies using the immunoradiometric assay (IRMA) comprised a compartmented enclosure containing multiple 96-well bendable polyvinylchloride (PVC) plates precoated with peptide according to the present invention at a concentration of 0.5 ug of peptide in 100 ul of pH 9.5 10 mM NaHCO$_3$ buffer per well and materials for radioimmunoassay including: (1) normal human serum (as negative control); (2) heat inactivated, NP40 solubilized AIDS serum (as positive control); (3) normal goat serum; and, (4) I$^{125}$ labeled goated anti human IgG. The procedure described in Example 3 is to be followed.

In this test kit, 96-well PVC plates precoated with the peptide of the present invention can be replaced by polystyrene beads precoated with the peptide of the present invention for use as the solid phase immunoadsorbent.

EXAMPLE 5A

A third test kit for detecting MTLV-III antibodies using the hemagglutination assay comprised a compartmented enclosure containing multiple 96-well U-shaped microplates and materials for hemagglutination assay including (1) a bottle of 21-mer peptide coated sheep red blood cells, gelatin particles or latex polystyrene beads; (2) normal human serum (as a negative control); and, (3) heat inactivated, NP40 solubilized AIDS positive serum (as positive control). The procedure described in Example 3A is to be followed.

EXAMPLE 6

An experiment was conducted to compare AIDS screening results using the method of Example 1 and heat inactivated, Np40 solubilized HTLV-III according to U.S. Pat. No. 4,520,113. Sera from normal subjects, patients with AIDS, ARC, were diluted (1:20 and 1:200). Duplicates of each diluted sera sample were tested against the peptide according the present invention and cultured HTLV-III according to U.S. Pat. No. 4,520,113. Normal human serum and heat inactivated HTLV-III reactive AIDS serum samples were used as control. The results are shown in Table III.

TABLE III

COMPARISON OF OD AT 492 nm OBTAINED BY USING PEPTIDE OF THE PRESENT INVENTION AND HEAT INACTIVATED NP40 SOLUBILIZED HTLV III AS SOLID PHASE IMMUNOADSORBENT

| Sample No. | Dilutions of Human Sera: Subjects | 1/20 (v:v) Peptide | 1/20 (v:v) HTLV-III | 1/200 (v:v) Peptide | 1/200 (v:v) HTLV-III |
|---|---|---|---|---|---|
|  | AIDS Control | over* | 1.64 ± .35 | over | 0.67 ± .08 |
|  | Normal Pooled Serum | 0.43 ± .02 | 0.35 ± .02 | 0.10 ± 0 | 0.08 ± 0 |
| 335 | AIDS | 1.51 ± .10 | 0.46 ± .02 | 0.23 ± .02 | 0.22 ± 0 |
| 336 | AIDS | 0.96 ± .08 | 0.45 ± .06 | 0.13 ± .01 | 0.15 ± .01 |
| 337 | NS** | 0.34 ± .02 | 0.21 ± .01 | 0.05 ± 0 | 0.05 ± .01 |
| 338 | NS | 0.30 ± 0 | 0.36 ± .04 | 0.08 ± .01 | 0.08 ± .01 |
| 339 | NS | 0.29 ± .03 | 0.29 ± .01 | 0.06 ± .01 | 0.07 ± .01 |
| 340 | AIDS | 1.65 ± .06 | 0.37 ± .03 | 0.22 ± .04 | 0.18 ± .01 |
| 341 | AIDS | over | 0.83 ± .05 | 0.36 ± .01 | 0.30 ± .01 |
| 344 | NS | 0.14 ± 0 | 0.14 ± .02 | 0.03 ± 0 | 0.07 ± .01 |
| 345 | AIDS | over | 0.62 ± .08 | 0.30 ± 0 | 0.25 ± 0 |
| 346 | AIDS | over | 1.72 ± .11 | 0.79 ± .01 | 0.48 ± .02 |
| 347 | AIDS | over | 0.54 ± .01 | 0.77 ± .04 | 0.22 ± 0 |
| 348 | AIDS | 1.70 ± .01 | 1.07 ± .01 | 0.23 ± .01 | 0.30 ± .01 |
| 349 | NS | 0.24 ± .01 | 0.26 ± 0 | 0.24 ± 0 | 0.10 ± .01 |
| 350 | AIDS | over | 1.35 ± .05 | over | 0.44 ± .04 |
| 351 | NS | 0.23 ± .01 | 0.25 ± 0 | 0.05 ± .01 | 0.10 ± .04 |
| 352 | NS | 0.24 ± .01 | 0.23 ± 0 | 0.04 ± .01 | 0.04 ± .01 |
| 356 | AIDS | 1.58 ± .16 | 0.73 ± .08 | 0.18 ± 0 | 0.26 ± .01 |
| 357 | AIDS | over | 0.42 ± .02 | 1.63 ± .02 | 0.20 ± .01 |
| 358 | AIDS | over | 1.50 ± .13 | over | 0.82 ± .08 |
| 359 | NS | 0.28 ± .01 | 0.22 ± .01 | 0.09 ± .01 | 0.08 ± .01 |
| 360 | NS | 0.10 ± .01 | 0.10 ± .01 | 0.02 ± .01 | 0.04 ± .03 |
| 361 | AIDS | over | 0.60 | 1.71 | 0.25 |

*over = OD$_{492nm}$ reading higher than 2.0
**NS = normal serum

The results in Table III show that the method is highly sensitive. The optical density achieved using the peptide of the present invention against duplicate AIDS sera samples at the same dilution is much higher than the optical density achieved using deactivated HTLV-III against identical sera samples at identical dilutions. Further, where the results with deactivated HTLV-III may be questionable, e.g. Example 335, 336, 340, 345, 347, 357 and 361 results with the peptide of the present invention is definitive, demonstrating the high degree of sensitivity and specificity of the method.

EXAMPLE 7

Four healthy Balb/c mice were bled and their sera tested according to the procedure of Examples 1 and 2. The results indicated that the Balb/c mice were free of antibodies to both HTLV-III and the 21mer peptide as shown in Table IV. The four mice were then separated into two groups A and B and immunized according to the following procedures.

GROUP A

Two of the Balb/c mice were injected with sucrose-banded HTLV-III virus mixed with an equal volume of complete Freund's adjuvant at 20 ug/0.2 ml/injection into multiple sites both intraperitoneally and subcutaneously. The immunization was repeated according to the following schedule:

|  | days |
|---|---|
| initial immunization | 0 |
| second immunization | 14 |
| third immunization | 21 |
| fourth immunization | 28 |
| fifth immunization | 35 |
| sixth immunization | 42 |

GROUP B

Two of the Balb/c mice were similarly injected with the 21mer peptide conjugated to human serum albumin (HSA), as the carrier protein, at 20 ug/20 ug HSA/0.2 ml/injection. The immunization schedule was also the same as that of Group A.

Bleedings were taken from both Group A and B after the sixth immunization and the sera analyzed by the procedures of Examples 1 and 2, except using horseradish peroxidase conjugated goat anti-mouse IgG as the tracer antibody. The results are shown in Table V.

The result indicate that the 21mer peptide represent a highly immunogenic epitope present on HTLV-III since sera obtained from mice previously immunized with HTLV-III contain high titer antibodies to HTLV-III as well as to the 21mer peptide. Furthermore, the 21mer peptide is a potent immunogen in eliciting the production of antibodies to HTLV-III in healthy mammals as demonstrated by the presence of high titer antibodies to HTLV-III in the sera obtained from mice previously immunized with the 21mer peptide coupled to Human Serum Albumin as a carrier protein.

It is quite remarkable that synthetic peptides representing minute fractions of a large virus can be manipulated to mimic the antigenic/immunogenic process to an extent that neutralizing or protective antibodies can be prepared from these synthetic peptides. The potential advantages in cost and safety of using the synthetic peptides, as vaccines make this approach a realistic expectation. The 21mer peptide, its analogues and segments, as described herein, have been found to represent highly immunogenic epitopes of HTLV-III in that the 21mer peptide, along with its conjugated forms, can elicit high titers of antibodies to HTLV-III has hereby been demonstrated and are, therefore, candidates for use as synthetic vaccines in mammals or humans to elicit specific antibodies to HTLV-III for protective purposes. It is also expected that polymeric forms of the 21mer peptide, its analogues and segments, will also be useful as candidates for synthetic vaccines for the same purposes.

TABLE IV

Unimmunized Normal Balb/C Mice $OD_{492}$

| Coating Antigen | Serum Titer | | | | | | |
|---|---|---|---|---|---|---|---|
|  | Undiluted | 1/10 | 1/100 | 1/1000 | 1/10,000 | 1/100,000 | B.G.* |
| HTLV-III (10 ug/ml) | 0.17 | 0.06 | 0.04 | 0.05 | 0.05 | 0.01 | 0.06 |
| 21mer (5 ug/ml) | 0.15 | 0.07 | 0.04 | 0.03 | 0.05 | 0.02 | 0.04 |

TABLE V

GROUP A
Balb/C Mice Immunized with HTLV-III Virus $OD_{492}$

| Coating Antigen | Serum Titer | | | | |
|---|---|---|---|---|---|
|  | 1/10 | 1/100 | 1/1000 | 1/10,000 | 1/100,000 |
| HTLV-III (10 ug/ml) | 2.0 | 2.0 | 0.76 | 0.25 | 0.16 |
| 21mer peptide (5 ug/ml) | 2.0 | 2.0 | 0.52 | 0.25 | 0.13 |

GROUP B
Balb/C Mice Immunized with 21mer peptide $OD_{492}$

| Coating Antigen | Serum Titer | | | | | |
|---|---|---|---|---|---|---|
|  | 1/10 | 1/100 | 1/500 | 1/1000 | 1/2500 | B.G.* |
| HTLV-III (10 ug/ml) | 2.24 | 1.64 | 0.97 | 0.75 | 0.56 | 0.05 |
| 21mer peptide (5 ug/ml) | 2.12 | 0.48 | 0.12 | 0.11 | 0.10 | 0.06 |

*B.G. = background

EXAMPLE 8

Eight analogues of the 21mer peptide and an overlapping 19mer peptide were prepared in their amide form according to the classical Merrifield method described herein above. The amino acid sequence of each of the analogues are shown in Table VI.

A serum sample from a patient diagnosed as having AIDS and previously determined to contain antibodies to HTLV-III was obtained. ELISA test according to Example 1 were conducted using each of the analogues as the coating antigen against the above AIDS serum sample. The reactivity of each of the analogues was compared with that of the 21mer peptide which was assigned a value of 100. The results are shown in Table VII.

The above examples illustrate various embodiments of the invention and are not to be taken as limiting the scope of the invention.

TABLE VI

| Peptide | Amino Acid Sequence | Relative % Reactivity |
|---|---|---|
| 1 | —Val—Trp—Gly—Ile—Lys—Gln—Leu—Gln—Ala—Arg—Ile—Leu—Ala—Val—Glu—Arg—Tyr—Leu—Lys— | 5 |
| 2 | —Gln—Leu—Gln—Ala—Arg—Ile—Leu—Ala—Val—Glu—Arg—Tyr—Leu—Lys— | 13.5 |
| 3 | —Arg—Ile—Leu—Ala—Val—Glu—Arg—Tyr—Leu—Lys— | 5 |
| 4 | —Arg—Ile—Leu—Ala—Val—Glu—Arg—Tyr—Leu—Lys— Asp—Gln—Gln—Leu—Leu—Gly—Ile— | 28.3 |
| 5 | —Ile—Leu—Ala—Val—Glu—Arg—Tyr—Leu—Lys— Asp—Gln—Gln—Leu—Leu—Gly—Ile— | 30.3 |
| 6 | —Arg—Ile—Leu—Ala—Val—Glu—Arg—Tyr—Leu—Lys— Asp—Gln—Gln—Leu—Leu—Gly—Ile—Trp—Gly—Cys—Ser— | 100 |
| 7 | —Arg—Leu—Ala—Val—Glu—Arg—Tyr—Leu—Lys— Asp—Gln—Gln—Leu—Leu—Gly—Ile—Trp—Gly—Cys—Ser— | 66.8 |
| 8 | —Val—Glu—Arg—Tyr—Leu—Lys— Asp—Gln—Gln—Leu—Leu—Gly—Ile—Trp—Gly—Cys—Ser— | 53.9 |
| 9 | —Lys— Asp—Gln—Gln—Leu—Leu—Gly—Ile—Trp—Gly—Cys—Ser— | 38.3 |
| 10 | — Asp—Gln—Gln—Leu—Leu—Gly—Ile—Trp—Gly—Cys—Ser— | 8 |
| 11 | —Ile—Leu—Ala—Val—Glu—Arg—Tyr—Leu—Lys— Asp—Gln—Gln—Leu—Leu—Gly—Ile—Trp—Gly—Cys—Ser— | 20.0 |

TABLE VII

Calculation of % Reactivity $$\overline{OD_{492}}^{*}$$

| Coating Peptide Concentration | 5 ug/ml | | 20 ug/ml | | 80 ug/ml | | Relative % Reactivity |
|---|---|---|---|---|---|---|---|
| Serum Dilution | 1/200 AIDS | 1/400 AIDS | 1/200 AIDS | 1/400 AIDS | 1/200 AIDS | 1/400 AIDS | $\sqrt{\dfrac{\sum_{i=1}^{6} \overline{OD_{492}}\, i^2}{6}}$ |
| Analog Peptide | i=1 | i=2 | i=3 | i=4 | i=5 | i=6 | i=6 |
| 6 | 1 | 1 | 1 | 1 | 1 | 1 | 100% |
| 7 | 0.60 | 0.64 | 0.67 | 0.70 | 0.73 | 0.66 | 66.8% |
| 8 | 0.45 | 0.49 | 0.59 | 0.53 | 0.63 | 0.53 | 53.9% |
| 9 | 0.21 | 0.20 | 0.38 | 0.39 | 0.53 | 0.50 | 38.9% |
| 10 | 0.01 | 0 | 0.07 | 0.04 | 0.14 | 0.11 | 8.0% |
| 11 | 0.12 | 0.09 | 0.23 | 0.21 | 0.28 | 0.23 | 20.0% |
| 4 | 0.34 | 0.25 | 0.30 | 0.24 | 0.31 | 0.24 | 28.3% |
| 5 | 0.30 | 0.22 | 0.30 | 0.26 | 0.40 | 0.31 | 30.3% |
| 3 | 0.01 | 0.02 | 0.01 | 0.01 | 0.07 | 0.06 | 3.9% |
| 2 | 0.01 | 0.02 | 0.06 | 0.05 | 0.25 | 0.20 | 13.5% |

$*\overline{OD_{492}} = \dfrac{OD_{492}\text{ reading on an Analog peptide coated well}}{OD_{492}\text{ reading on 21mer peptide coated well}}$

We claim:

1. Peptide composition having specific immunoreactivity to antibodies to HTLV-III selected from the group consisting of peptide containing from twelve to twenty-five amino acids, the sequence of which corresponds to a part or the entirety of the following sequence:

Arg-Ile-Leu-Ala-Val-Glu-Arg-Tyr-Leu-Lys-Asp-Gln-Gln-Leu-Leu-Gly-Ile-Trp-Gly-Cys-Ser;

analogues thereof wherein the amino acids in the sequence are substituted, deleted or added as long as the immunoreactivity to antibodies to HTLV-III derived from the three dimensional conformation of the sequence is preserved; and conjugates of the peptides or analogues thereof, wherein:

Ala=alanine,
Arg=arginine,
Cys=cysteine
Gln=glutamine,
Glu=glutamic acid,
Gly=glycine,
Ile=isoleucine,
Leu=leucine,
Lys=lysine,
Ser=serine,
Trp=tryptophan,
Tyr=tyrosine, and
Val=valine.

2. A peptide composition according to claim 1 wherein the peptide is:

Arg-Ile-Leu-Ala-Val-Glu-Arg-Tyr-Leu-Lys-Asp-Gln-Gln-Leu-Leu-Gly-Ile-Trp-Gly-Cys-Ser.

3. An immunoassay method for the detection of antibodies to HTLV-III and diagnosis of AIDS, ARC or pre-AIDS conditions comprising:

(a) coating a solid support with an effective amount of the peptide composition according to claim 1 as an antigen;
b. adding a test sera diluted with a buffer wherein the antibodies to HTLV-III in the test sera form a peptide-antibody complex with the peptide composition;
c. incubating the mixture at room temperature; and
d. detecting the presence of the peptide-antibody complex.

4. An immunoassay method according to claim 3 wherein the solid support is coated with peptide having twenty-one amino acids in a sequence:

Arg-Ile-Leu-Ala-Val-Glu-Arg-Tyr-Leu-Lys-Asp-Gln-Gln-Leu-Leu-Gly-Ile-Trp-Gly-Cys-Ser.

5. An immunoassay method according to claim 3 wherein step d. comprises: introducing a second known antibody labelled with an enzyme and a substrate which reacts with the enzyme to a form colored product.

6. An immunoassay method according to claim 2 wherein step d. comprises: introducing a second known antibody labelled with a radioactive element.

7. An immunoassay method according to claim 3 wherein the peptide-antibody complex is detectable as an agglutination.

8. An immunoassay method according to claim 5 wherein for each assay procedure, the amount of the peptide composition is about 0.1 ug to about 20 ug of the peptide in a buffer of about pH 7 to 10.

9. An immunoassay method according to claim 5 wherein for each assay procedure, the amount of the peptide composition is about 1 ug of the peptide in a buffer of about pH 7 to 10.

10. An immunoassay method according to claim 6 wherein for each assay procedure, the amount of the peptide composition is about 0.1 ug to about 20 ug of the peptide in a buffer of about pH 7 to 10.

11. An immunoassay method according to claim 6 wherein for each assay procedure, the amount of the peptide composition is about 1 ug of the peptide in a buffer of about pH 7 to 10.

12. A test kit for the detection of antibodies to HTLV-III and the diagnosis of AIDS, ARC and pre-AIDS conditions comprising:

a. a solid support;
b. coating onto the solid support, an immunoadsorbent comprising a peptide composition according to claim 1
c. a sample of normal serum as negative control;
d. a sample of serum containing antibodies to HTLV-III as positive control; and e. a buffer for diluting the serum samples.

13. A test kit according to claim 12 wherein the immunoadsorbent is a peptide of twenty-one amino acids with a sequence:

Arg-Ile-Leu-Ala-Val-Glu-Arg-Tyr-Leu-Lys-Asp-Gln-Gln-Leu-Leu-Gly-Ile-Trp-Gly-Cys-Ser.

14. A test kit according to claim 12 further comprising:
    f. an enzyme labelled second antibody for binding with the peptide-antibody complex;
    g. a substrate which reacts with the enzyme labelled antibody to form a colored product; and
    h. a second buffer solution for stopping the development of the colored product.

15. A test kit according to claim 12 further comprising:
    f. a radioactive element labelled second antibody for binding with the peptide-antibody complex to detect the peptide-antibody complex.

16. A peptide which is specifically immunoreactive with antibodies to HTLV-III with not more than twenty-five amino acids in a sequence having as a segment thereof selected from the group consisting of:
    (a) -Trp-Gly-Cys-Ser;
    (b) -Lys-Asp-Gln-Gln-Leu-Leu-Gly-Ile; and
    (c)   Arg-Ile-Leu-Ala-Val-Glu-Arg-Tyr-Leu-Lys-Asp- wherein Trp=tryptophan, Gly=glycine, Cys=cysteine, Ser=serine, Asp=Aspartic acid, Glu=glutamine, Leu=leucine, Ile=isoleucine, Ala=alanine, Val=valine, Glu=glutamic acid, Arg=arginine, Tyr=Tyrosine and Lys=lysine.

17. A peptide composition according to claim 16 wherein the peptide comprises at least fifteen amino acids.

* * * * *